US00PP08803P

United States Patent [19]

Fuess

[11] Patent Number: Plant 8,803

[45] Date of Patent: Jun. 28, 1994

[54] CHRYSANTHEMUM PLANT NAMED EMPIRE SERENADE

[76] Inventor: Janet S. Fuess, 22 Country Club Dr., New York Mills, N.Y. 13417

[21] Appl. No.: 445

[22] Filed: Jan. 4, 1993

[51] Int. Cl.[5] ..... A01H 5/00

[52] U.S. Cl. ..... Plt./76

[58] Field of Search ..... Plt. 76

*Primary Examiner*—Howard J. Locker

*Attorney, Agent, or Firm*—Foley & Lardner

[57] ABSTRACT

A Chrysanthemum plant named Empire Serenade particularly characterized by its flat capitulum form; decorative capitulum type; red-purple to greyed-purple ray floret color; diameter across face of capitulum of 51 to 64 mm when fully opened; branching pattern is spreading and prolific, with 8 breaks after pinch when grown outside under natural daylength in fall flowerings; natural season flower dat of August 27 when planting rooted cuttings on Jun. 25, 1992 in Salinas, Calif., and of September 21 to 28 when planting rooted cuttings June 15 to June 18 in Hightstown, N.J. in 1990 and 1991; not recommended for no light/no shade programs in spring; plant height of 28 to 36 cm when grown in fall under natural daylength with no growth regulators; and durable, uniform performance.

3 Drawing Sheets

The present invention comprises a new and distinct cultivar of Chrysanthemum, botanically known as *Dendranthema grandiflora*, and referred to by the cultivar name Empire Serenade.

Empire Serenade, identified as 8465 (N88-1), was originated from a cross made by Janet S. Fuess in a controlled breeding program in New Hartford, N.Y. in October 1987.

The female parent of Empire Serenade was the cultivar identified as Pink Champagne, disclosed in U.S. Plant Pat. No. 6,290, and described as a lavender-pink decorative garden mum.

The male parent of Empire Serenade was an unnamed seedling, identified as A85-39, and described as a deep pink decorative garden mum.

Empire Serenade was discovered and selected as one flowering plant within the progeny of the stated cross by Janet S. Fuess in August 1988 in New Hartford, N.Y.

The first act of asexual reproduction of Empire Serenade was accomplished when vegetative cuttings were taken from the initial selection in October 1988 in a controlled environment in New Hartford, N.Y. by Janet S. Fuess.

Horticultural examination of controlled flowerings of successive plantings has shown that the unique combination of characteristics as herein disclosed for Empire Serenade are firmly fixed and are retained through successive generations of asexual reproduction.

Empire Serenade has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October.

The following traits have been repeatedly observed and are determined to be basic characteristics of Empire Serenade, which, in combination, distinguish this Chrysanthemum as a new and distinct cultivar:

1. Flat capitulum form.

2. Decorative capitulum type.
3. Red-purple to greyed-purple ray floret color.
4. Diameter across face of capitulum of 51 to 64 mm when fully opened.
5. Branching pattern is spreading and prolific, with 8 breaks after pinch when grown outside under natural daylength in fall flowerings.
6. Natural season flower date of Aug. 27 when planting rooted cuttings on Jun. 25, 1992 in Salinas, Calif., and of Sep. 21 to 28 when planting rooted cuttings Jun. 15 to Jun. 18 in Hightstown, N.J. in 1990 and 1991.
7. Not recommended for no light/no shade programs in spring.
8. Plant height of 28 to 36 cm when grown in fall under natural daylength with no growth regulators.
9. Durable, uniform performance.

The accompanying photographic drawings show typical inflorescence and leaf characteristics of Empire Serenade, with the colors being as nearly true as possible with illustrations of this type.

Sheet 1 is a color photograph of Empire Serenade grown in natural season outside conditions in Salinas, Calif.

Sheet 2 is a black and white photograph of three views of the inflorescence of Serenade.

Sheet 3 is a black and white photograph showing the upper and under sides of the leaves of Empire Serenade at 3 stages of development (mature, intermediate and immature). In sheets 2 and 3 a measuring tape in centimeters has been added.

Of the commercial cultivars known to the inventor, the most similar in comparison to Serenade is the cultivar Debonair disclosed in U.S. Plant Pat. No. 5,324. Reference is made to attached Chart A, which compares certain characteristics of Empire Serenade to the same characteristics of Debonair.

Similar traits are capitulum form and type, natural season flower date and plant height. The ray floret color of Empire Serenade is a unique red-purple to greyed purple, while the ray floret color of Debonair is purple. Empire Serenade has a slightly smaller diameter of capitulum and a more prolific branching pattern when compared with Debonair. In addition, Empire Serenade is not recommended for no light/no shade spring programs, while Debonair is recommended for these programs.

In the following description color references are made to The Royal Horticultural Society Colour Chart. The actual color of Empire Serenade is not represented in The RHS Color Chart, and the values given are those believed closest to the color of Empire Serenade. The color values were determined on plant material grown as a pinched garden mum grown outdoors in Salinas, Calif. on Sep. 14, 1992.

Classification:

*Botanical.*—*Dendranthema grandiflora* cv Empire Serenade.

*Commercial.*—Flat decorative garden mum.

INFLORESCENCE

A. Capitulum:

*Form.*—Flat.

*Type.*—Decorative.

*Diameter across face.*—51 to 64 mm when fully opened.

B. Corolla of ray florets:

*Color (general tonality from a distance of three meters).*—Red-purple.

*Color (upper surface).*—Between 59C and 186B.

*Color (under surface).*—Base 4C to 4D, overlaid and streaked with 59C.

*Shape.*—Cross-section convex, longitudinal section of outer rays slightly convex.

C. Corolla of disc florets:

*Color (mature).*—6B.

*Color (immature).*—6tinged with 151D.

D. Reproductive organs:

*Androecium.*—Present on disc florets only; scant pollen.

*Gynoecium.*—Present on both ray and disc florets.

PLANT

A. General appearance:

*Height.*—28 to 36 cm when grown in fall under natural daylength with no growth regulators.

*Branching pattern.*—Spreading and prolific, with 8 breaks after pinch when grown outside under natural daylength in fall flowerings, compared to 5–8 lateral breaks for Debonair when grown under similar conditions.

B. Foliage:

*Color (upper surface).*—147A.

*Color (under surface).*—147B.

*Shape.*—See photograph.

CHART A

| CULTIVAR | Empire SERENADE | DEBONAIR |
|---|---|---|
| Ray floret color | Red-purple to greyed-purple (Between 59C and 186B) | Purple (78D) |
| Capitulum form and type | Flat Decorative | Flat Decorative |
| Diameter across face of capitulum | 51 to 64 mm | 64 to 70 mm |
| Branching pattern | Spreading and prolific (8 laterals after pinch) | Spreading (5–8 laterals after pinch) |
| Nat. season flower date: | | |
| in Salinas, CA | Aug 27 | Aug 26 to 31 |
| in Hightstown, NJ | Sep 21 to 28 | Sep 24 to 30 |
| Plant height: | | |
| in natural season fall | 28 to 36 cm | 30 to 38 cm |

COMPARISONS MADE OF PLANTS GROWN AS UNDER NATURAL SEASON OUTDOOR CONDITIONS IN SALINAS, CALIFORNIA AND IN HIGHTSTOWN, NEW JERSEY

I claim:

1. A new and distinct Chrysanthemum plant named Empire Serenade, as described and illustrated.

* * * * *

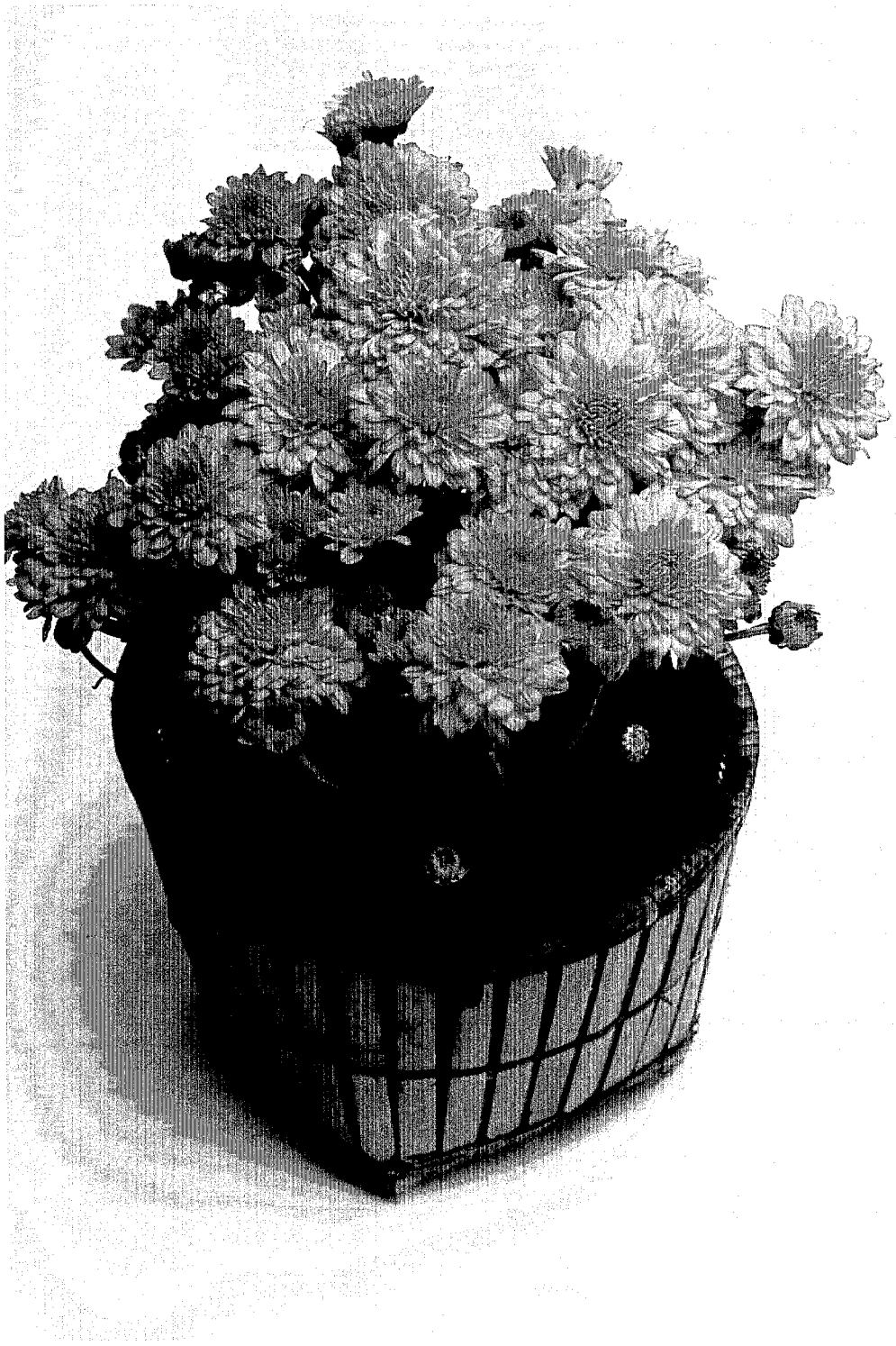

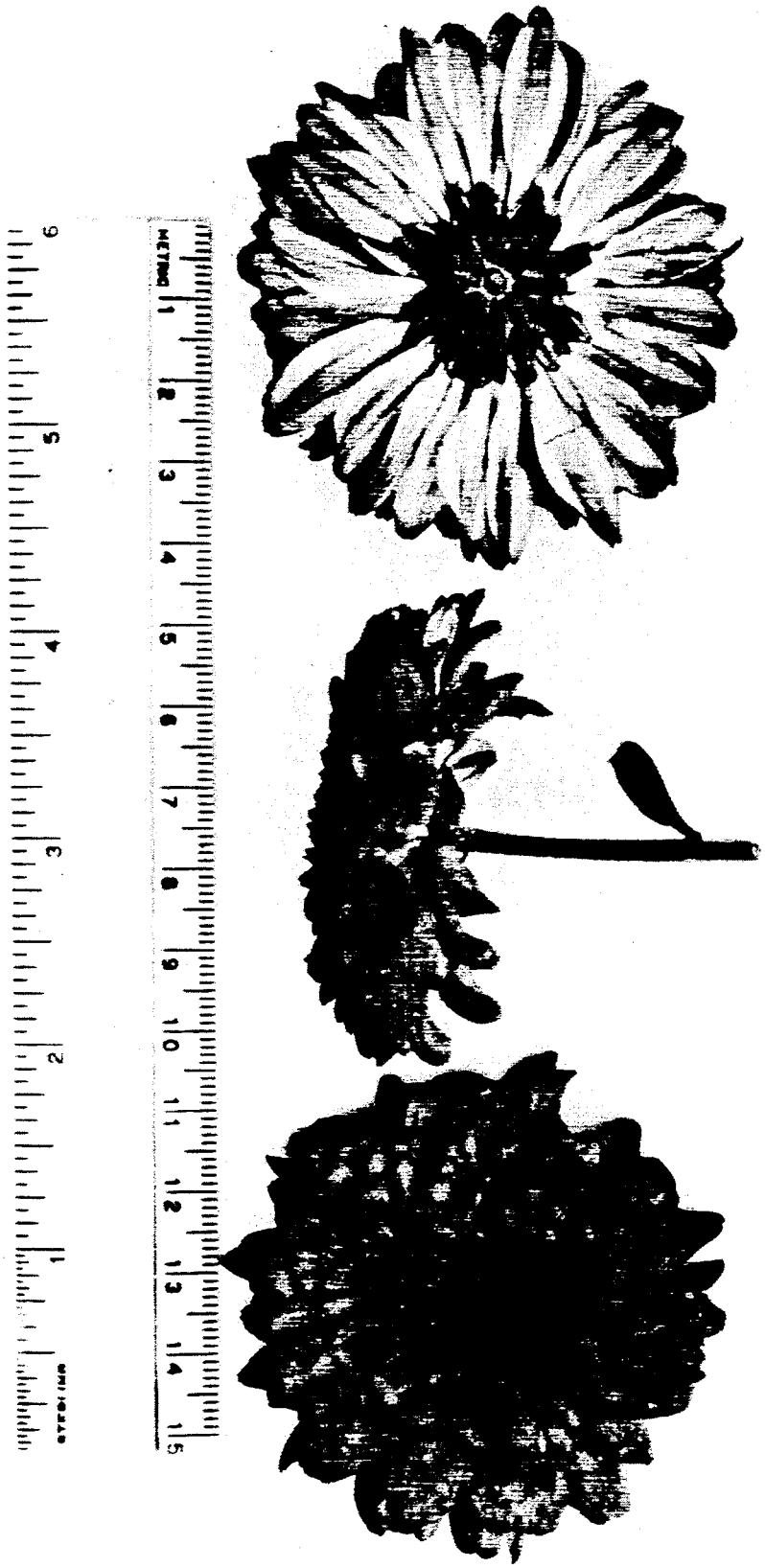

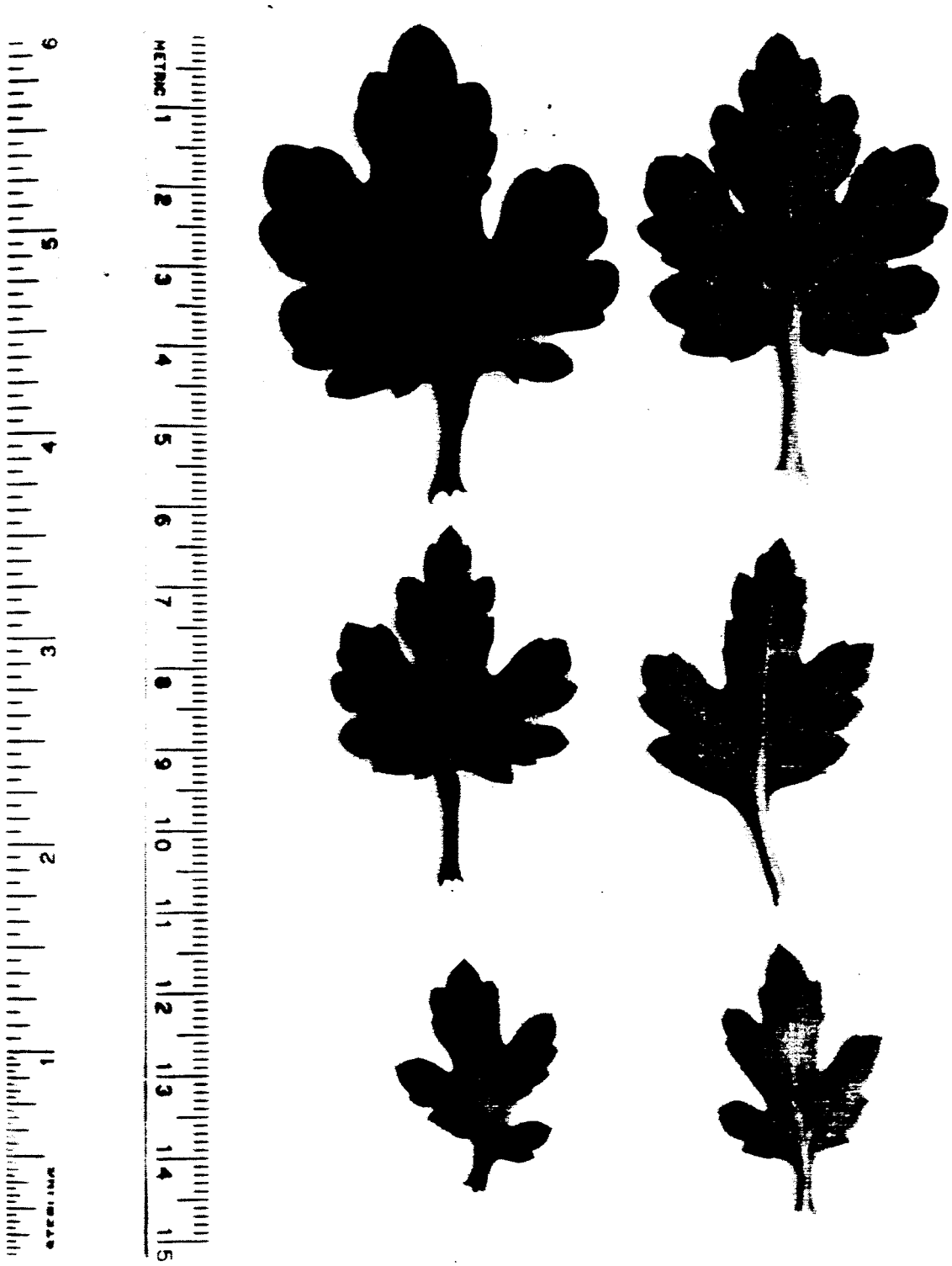
METRIC
INCHES

UNITED STATES PATENT AND TRADEMARK OFFICE

CERTIFICATE OF CORRECTION

PATENT NO. : Plant 8,803

DATED : June 28, 1994

INVENTOR(S) : Janet M. FUESS

It is certified that error appears in the above-indentified patent and that said Letters Patent is hereby corrected as shown below:

Column 3, line 34, "6tinged" should read --6B tinged--.

Signed and Sealed this

Eighteenth Day of October, 1994

*Attest:*

*Attesting Officer*

Bruce Lehman

BRUCE LEHMAN

*Commissioner of Patents and Trademarks*